United States Patent [19]

Schmitt

[11] Patent Number: 4,528,383

[45] Date of Patent: Jul. 9, 1985

[54] SUBSTITUTED CYCLIC AND HETEROCYCLIC METHANE SULFONATES

[75] Inventor: Kirk D. Schmitt, Pennington, N.J.

[73] Assignee: Mobil Oil Corporation, New York, N.Y.

[21] Appl. No.: 373,553

[22] Filed: Apr. 30, 1982

[51] Int. Cl.$^3$ ............... C07D 307/12; C07D 333/18; C07D 207/08

[52] U.S. Cl. .................. 549/78; 166/274; 166/275; 252/8.55 D; 260/501.13; 260/503; 260/936; 548/570; 549/502; 568/12

[58] Field of Search .................. 549/78, 502

[56] References Cited

U.S. PATENT DOCUMENTS

| | | | |
|---|---|---|---|
| 3,424,770 | 1/1969 | Stein et al. | 260/400 |
| 3,455,956 | 7/1969 | Hirano et al. | 549/78 X |
| 3,645,665 | 2/1972 | Etters | 549/502 X |
| 3,682,965 | 8/1972 | Hickner et al. | 71/88 X |
| 3,772,444 | 11/1973 | Sarett et al. | 549/78 X |
| 3,875,187 | 4/1975 | Hickner et al. | 260/347.2 |
| 3,939,911 | 2/1976 | Maddox, Jr. et al. | 166/274 |
| 4,008,766 | 2/1977 | Savins | 166/273 |
| 4,051,151 | 9/1977 | Tsuchihashi et al. | 549/502 X |
| 4,126,746 | 11/1978 | Hickner et al. | 544/219 |
| 4,193,452 | 3/1980 | Wilson et al. | 166/274 |
| 4,267,123 | 5/1981 | Chen et al. | 260/501.12 |
| 4,340,543 | 7/1982 | Koda et al. | 549/502 X |
| 4,469,607 | 9/1984 | Schmitt | 260/501.13 X |
| 4,487,702 | 12/1984 | Schmitt | 252/8.55 D |

FOREIGN PATENT DOCUMENTS 0037699 10/1981 European Pat. Off. .
1069379 5/1967 United Kingdom ............. 549/78

OTHER PUBLICATIONS

Reed et al., "Improved Oil Recovery by Surfactant and Polymer Flooding", pp. 383-437, (1977), Academic Press.
Falcone et al., J. A. O. C. S., 59, (No. 10), Oct. 1982, pp. 826A-832A.
Krumrine et al., Surfactant Flooding 1: The Effect of Alkaline Additives on IFT, Surfactant Adsorption, and Recovery Efficiency", pp. 217-222.

Primary Examiner—Joseph Paul Brust
Attorney, Agent, or Firm—Alexander J. McKillop; Michael G. Gilman; Charles J. Speciale

[57] ABSTRACT

There are provided compounds which are alkyl sulfonates substituted on a 5-membered heterocyclic or cyclic ring. The hetero-substituents of the ring may be O, S, $R_2N$, $R_3R_4{}^+N<$,

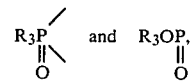

where $R_2$, $R_3$ and $R_4$ are the same or different substituted or unsubstituted, and are hydrogen, alkyl or aryl. Optionally, the hetero-substituent may be replaced by $R_3R_4C$. The alkyl sulfonate substituent is in the 3 position of the ring and a substituted or unsubstituted alkyl substituent is in the 4 position of the ring. The compounds may be prepared by reacting $X(CH_2CH=CHR)_2$, where X is the above mentioned hetero-substituents or $R_3R_4C<$, with a bisulfite salt.

3 Claims, 2 Drawing Figures

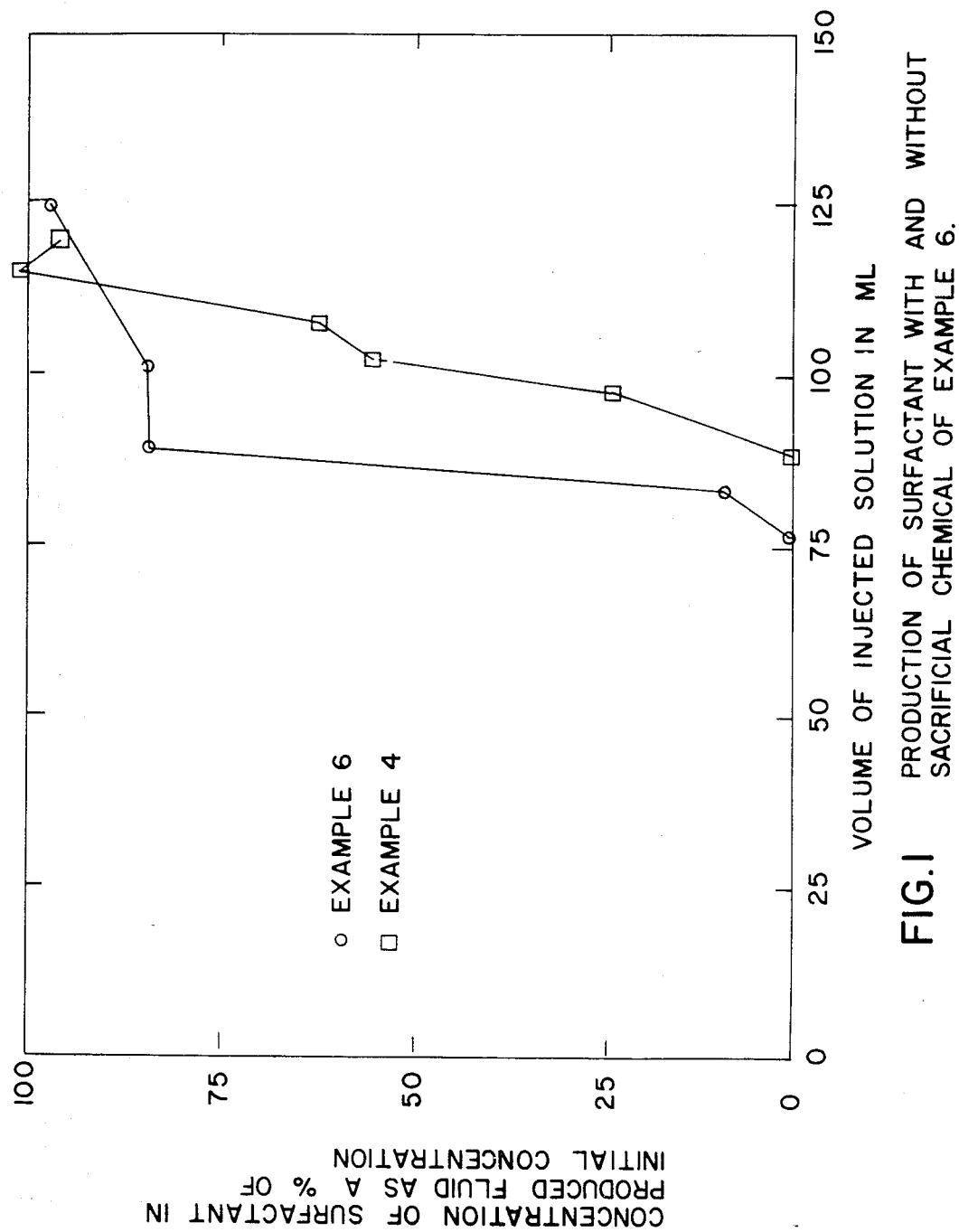
FIG.1 PRODUCTION OF SURFACTANT WITH AND WITHOUT SACRIFICIAL CHEMICAL OF EXAMPLE 6.

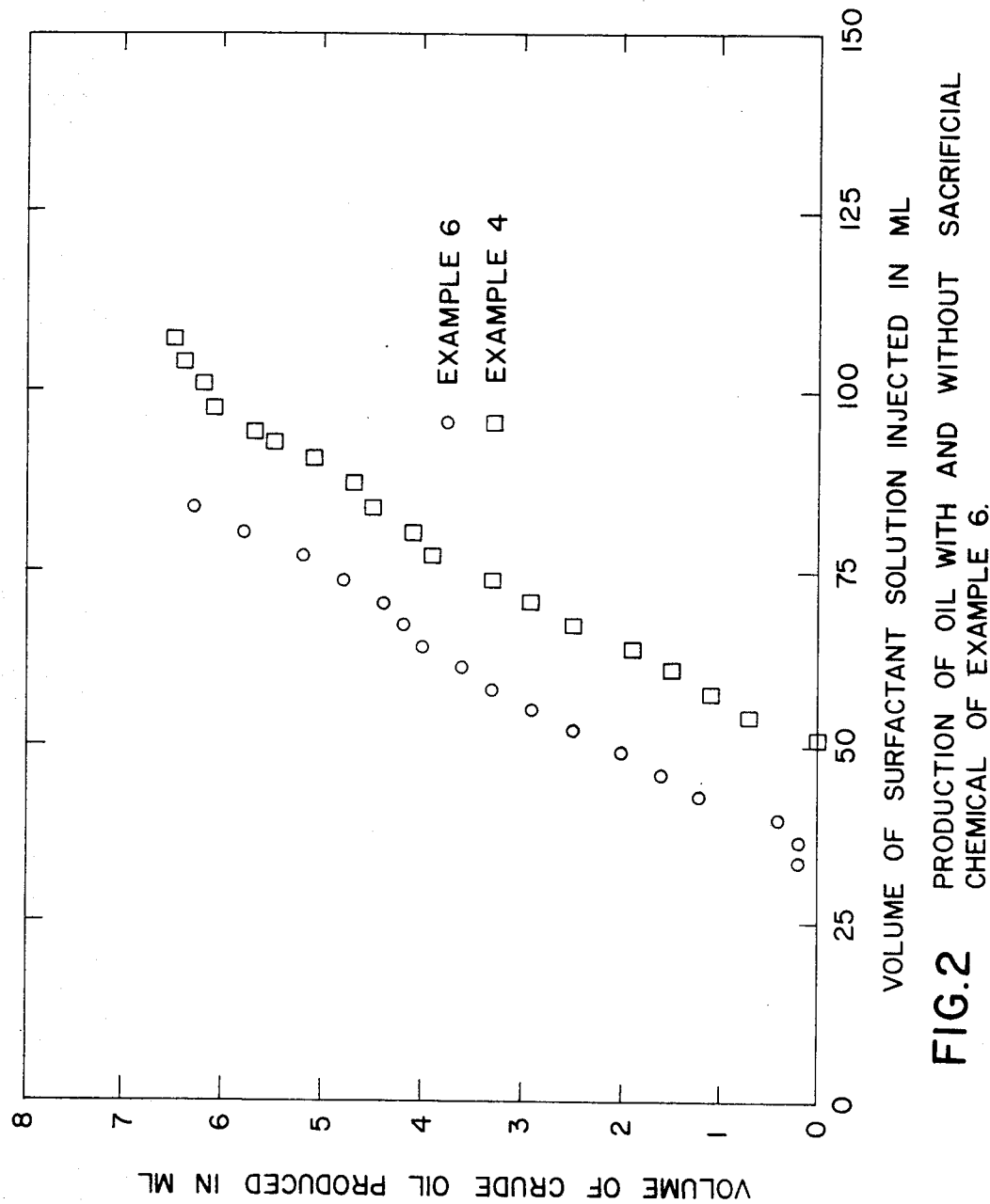
FIG. 2 PRODUCTION OF OIL WITH AND WITHOUT SACRIFICIAL CHEMICAL OF EXAMPLE 6.

SUBSTITUTED CYCLIC AND HETEROCYCLIC METHANE SULFONATES

BACKGROUND OF THE INVENTION

This invention is directed to substituted cyclic and heterocyclic methane sulfonates.

The reaction of olefins with alkali metal bisulfite, in which the bisulfite adds across the double bond, is known. [M. S. Kharasch, E. M. May, F. R. Mayo, J. Org. Chem., 3, 175 (1938)]. The use of cosolvents [Norton et al, U.S. Pat. No. 3,522,297] and initiators [C. F. Norton, N. F. Seppi, and M. J. Reuter, J. Org. Chem., 33, 4158 (1968)] to promote this reaction is also known as is the use of a certain amount of final sulfonate product as solubilizer in those cases where the olefin is not water soluble [Chen et al U.S. Pat. No. 4,267,123].

It has been discovered, quite unexpectedly, that the course of the reaction is different when two double bonds are present in the same molecule in the relationship $X(CH_2CH=CHR)_2$, where X is as defined hereinafter. By way of illustration, it is known that allyl alcohol produces sodium 3-hydroxypropane sulfonate in high yield when treated with sodium bisulfite, air, and water. [R. F. Fischer, Ind. and Eng. Chem., 56, 41 (1964)]. This reaction is illustrated as follows.

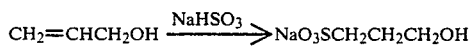

$$CH_2=CHCH_2OH \xrightarrow{NaHSO_3} NaO_3SCH_2CH_2CH_2OH$$

It would be expected that similar treatment of diallyl ether with two or more moles of bisulfite would lead to a disulfonate ether product as follows.

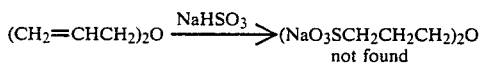

$$(CH_2=CHCH_2)_2O \xrightarrow{NaHSO_3} (NaO_3SCH_2CH_2CH_2)_2O$$
not found

Instead, however, there is produced the unexpected tetrahydrofuran derivative as follows.

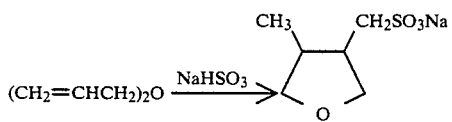

SUMMARY OF THE INVENTION

According to one aspect of the present invention, there is provided an ion of the formula

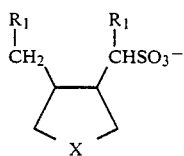

wherein:
(i) X is selected from the group consisting of O, S, $R_2N<$, $R_3R_4C<$, $R_3R_4{}^+N<$,

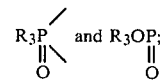

$R_3P<$ and $R_3OP$;

and (ii) $R_1$, $R_2$, $R_3$ and $R_4$ are the same or different, are substituted or unsubstituted and are selected from the group consisting of hydrogen, alkyl and aryl.

$R_1$ and $R_2$ are selected from hydrogen and substituted or unsubstituted $C_1$–$C_3$ alkyl, and $R_3$ and $R_4$ are selected from hydrogen, substituted or unsubstituted $C_1$–$C_{16}$ alkyl and substituted or unsubstituted $C_6$–$C_{20}$ aryl.

According to another aspect of the invention, there is provided compounds containing a cation and an anion of the above formula.

According to another aspect of the invention, there is provided a method of making such compounds.

BRIEF DESCRIPTION OF THE DRAWINGS

FIG. 1 presents the graphical relationship between the volume of surfactant solution injected with and without sacrificial agent and the concentration of surfactant in produced fluid in percent of initial concentration.

FIG. 2 presents the graphical representation between the volume of surfactant injected with and without sacrificial agent and the volume of oil produced.

DESCRIPTION OF SPECIFIC EMBODIMENTS

The compounds of this invention are readily prepared by reacting a bisulfite salt and air or oxygen with a diallyl compound, having the formula $X(CH_2CH=CHR)_2$, in an aqueous phase. The reaction proceeds generally at ambient conditions of temperature and pressure, although higher temperatures and pressures may be used if desired. The reaction is carried out in a homogenous aqueous phase. This phase can be water alone, if the olefinic reactant is water soluble. If not, this phase will be a mixture of water and sufficient cosolvent, such as $C_1$–$C_4$ alkanol to dissolve the olefinic reactant.

The bisulfite salt reactant may be any such reactable bisulfite salt such as sodium bisulfite, lithium bisulfite, potassium bisulfite, and ammonium bisulfite. This bisulfite salt may, thus, have the formula $MHSO_3$, where M is Na, Li, K or ammonium.

An oxygen containing gas acts as an initiator. It can be oxygen or air or other molecular oxygen containing gas.

The organic compound starting reactant for preparing the compounds of this invention has the structure, $X(CH_2CH=CHR_1)_2$, wherein X and $R_1$ are as defined as herein. When X is $R_3R_4C$ many routes exist for preparing the starting reactant. For example, where $R_1=R_3=R_4$ the preparation is known (J. Chem. Soc., 1950, 3131). A route using readily available chemicals and known reactions can be as follows:

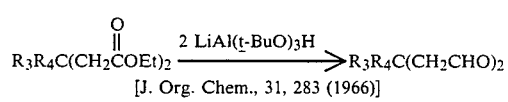

$$R_3R_4C(CH_2COEt)_2 \xrightarrow{2\ LiAl(\underline{t}\text{-}BuO)_3H} R_3R_4C(CH_2CHO)_2$$
[J. Org. Chem., 31, 283 (1966)]

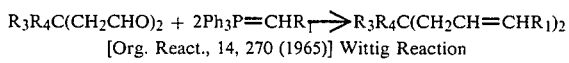

$$R_3R_4C(CH_2CHO)_2 + 2Ph_3P=CHR_1 \longrightarrow R_3R_4C(CH_2CH=CHR_1)_2$$
[Org. React., 14, 270 (1965)] Wittig Reaction Where X is $R_3R_4N^+<$, if $R_3=R_4=H$, the reactant is commercially available diallyl amine. Compounds where $R_3$ and $R_4$ may not both be H can be prepared by appropriate alkylation reactions, e.g.,

$$R_3NH_2 + 2\ ClCH_2CH=CHR_1 \longrightarrow$$

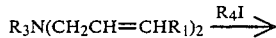

$$R_3N(CH_2CH=CHR_1)_2 \xrightarrow{R_4I}$$

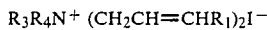

$$R_3R_4N^+ (CH_2CH=CHR_1)_2 I^-$$

Compounds in which $X=O$ or $S$ and $R_1=H$ are readily available diallyl ether and diallyl thioether. Other ethers are available by the reaction:

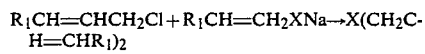

$$R_1CH=CHCH_2Cl + R_1CH=CH_2XNa \rightarrow X(CH_2CH=CHR_1)_2$$

in which $X=O$ or $S$. $R_1CH=CHCH_2XH$ is easily made by reacting $R_1CH=CHCH_2Cl$ with aqueous NaOH or KOH.

When

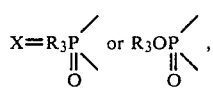

$$X=R_3\overset{\overset{\displaystyle \diagup}{\|}}{\underset{O}{P}} \text{ or } R_3O\overset{\overset{\displaystyle \diagup}{\|}}{\underset{O}{P}},$$

the reactant can be made as follows:

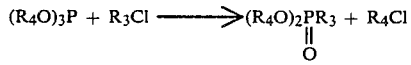

$$(R_4O)_3P + R_3Cl \longrightarrow (R_4O)_2P\overset{\|}{\underset{O}{R_3}} + R_4Cl$$

Arbusov Reaction

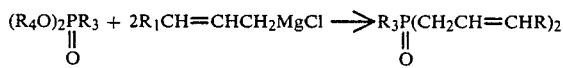

$$(R_4O)_2P\overset{\|}{\underset{O}{R_3}} + 2R_1CH=CHCH_2MgCl \longrightarrow R_3\overset{\|}{\underset{O}{P}}(CH_2CH=CHR_1)_2$$

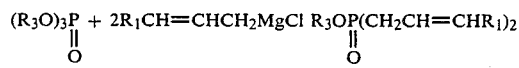

$$(R_3O)_3P + 2R_1CH=CHCH_2MgCl \quad R_3O\overset{\|}{\underset{O}{P}}(CH_2CH=CHR_1)_2$$

(I. O. Sutherland, "Comprehensive Organic Chemistry", Volume 2, Pergamon Press, Oxford, England, 1979, page 1177).

The following examples illustrate the conditions which give rise to compounds of this invention with a number of different "X" substitutions.

EXAMPLE 1

A solution of 31.9 g. of $NaHSO_3$ in 170 ml. $H_2O$ was added dropwise over 15 min. to a room temperature solution containing 15 g. diallyl ether, 150 ml. $H_2O$, and 150 ml. ethanol while air was bubbled through at about 15 ml./min. An exothermic reaction took the temperature to 40° C. The mixture was evaporated to dryness, extracted with ethanol in a Soxhlet extractor and the ethanol soluble material recrystallized from methanol to give 21.7 g. (72%) white crystals whose elemental analysis was consistent with a mixture of cis and trans isomers of the formula

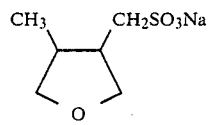

where the cis and trans configuration is with respect to the bond between the 3 and 4 carbon atoms. The theoretical elemental analysis for $C_6H_{11}NaO_4S$ is as follows: C,35.63%; H,5.48%; Na,11.37%; S,15.86%. The following was actually found: C,35.51%; H,5.41%; Na,11.47%; S,15.89%.

The Carbon-13 NMR showed two isomers in ratio 3:1 of six carbons each. The chemical shifts were consistent with cis and trans tetrahydrofurans derivatives of the above formula. The proton multiplicities indicated by the single frequency off resonance decoupled spectrum indicated that each carbon had the correct number of protons for the structures drawn.

| | Carbon 13-NMR Data | | | |
|---|---|---|---|---|
| | cis-isomer | | trans-isomer | |
| Carbon | Shift* | Multiplicity | Shift* | Multiplicity |
| $CH_3$ | 12.3 | q | 14.8 | q |
| $CH_2SO_3$ | 49.2 | t | 52.7 | t |
| 1 | 70.3 | t | 72.4 | t |
| 2,3 | 37.6,35.1 | d,d | 42.1,38.6 | d,d |
| 4 | 74.2 | t | 73.6 | t |

*Relative to $(CH_3)_3SiCH_2CH_2CH_2SO_3Na$ as O.

The major isomer was assigned the cis structure because of the relative upfield shifts of its $-CH_2SO_3$ and $CH_3-$ carbons. Substituents located cis nearly always show carbon NMR shifts upfield of trans substituents in olefins, cyclohexanes, and cyclopentanes.

[R. A. Friedel and H. L. Retcotsky, J. Amer. Chem. Soc., 85, 1300 (1963); D. K. Dalling and D. M. Grant, ibid, 89,6612 (1967); and M. Chrisrl, H. J. Reich, and J. D. Roberts, ibid, 93, 3463 (1971).]

EXAMPLE 2

A mixture of 15 g. diallylamine, 150 ml. water and 150 ml. t-butyl alcohol at 4° C. was treated with 16.1 g. $NaHSO_3$ and 1 g. $Na_2SO_3$ as in Example 1. After 30 minutes the inorganic salts were filtered off and the reaction mixture stripped to give 30.5 g. (98%) of a white solid whose C-13 NMR showed it to be a 9:1 mixture of cis- and trans pyrrolidines of the formula

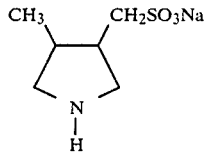

where the cis and trans configuration is with respect to the bond between the 3 and 4 carbon atoms.

| | Carbon 13-NMR Data | | | |
|---|---|---|---|---|
| | cis-isomer | | trans-isomer | |
| Carbon | Shift* | Multiplicity | Shift* | Multiplicity |
| $CH_3$ | 13.0 | q | 14.9 | q |
| $CH_2SO_3$ | 48.2 | t | 53.3,50.8 | t |
| 1,4 | 52.2,50.3 | t,t | 51.7 | t,t |

-continued

| | Carbon 13-NMR Data | | | |
| --- | --- | --- | --- | --- |
| | cis-isomer | | trans-isomer | |
| Carbon | Shift* | Multiplicity | Shift* | Multiplicity |
| 2,3 | 38.0,35.3 | d,d | 41.9,38.3 | d,d |

*Relative to $(CH_3)_3SiCH_2CH_2CH_2SO_3NA$ as O.

The major isomer is, assigned the cis configuration because of the relative upfield positions of its $CH_3$ and $-CH_2SO_3^-$ resonances.

EXAMPLE 3

A room temperature solution of 225 ml. $H_2O$, 225 ml. t-butyl alcohol and 43.2 g. diallylhexadecylmethylammonium iodide was stirred under a flow of 2 ml./min. air and a mixture of 34.2 g. $NaHSO_3$ and 9.8 g. $Na_2SO_3$ in 150 ml. $H_2O$ added over 2 hours. Nitrogen-14 NMR of the starting solution indicated a single peak at $-313$ ppm ($NO_3^- = O$ PPM). Nitrogen-14 NMR of the reaction mixture at 2 hours indicated 90% conversion to another compound with a chemical shift of $-305$ ppm. After purification by chromatography on a Water's Associates Prep 500 liquid chromatograph there were obtained 20.6 g. white wax (53%) whose elemental analysis was consistent with the expected pyrrolidinium sulfonate of the following structure:

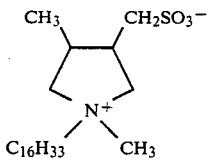

Calculated for $C_{23}H_{47}NSO_3$: C,66.13%; H,11.34%; N,3.35%; S,7.68%. Found: C,66.00%; H,10.53%; N,3.33%; S,7.34%.

The process described has obvious utility in synthesis of the compounds described. The compounds made by the process are new, useful compositions of matter in enhanced recovery of oil. The particular utility of these compounds in this regard depends primarily on their molecular weight. Low molecular weight compounds of this invention, e.g., where X=O,S,NH and $R_1=H$, tend to be most useful as sacrificial chemicals in enhanced oil recovery fluids. Higher molecular weight compounds, e.g., particularly those where $X=R_3R_4^+N<$ and where $R_3$ plus $R_4$ have more than 10 carbon atoms, tend to be most useful as brine tolerant surfactants. These particular utilities are discussed more fully hereinafter.

SACRIFICIAL AGENTS

In the recovery of oil from oil-bearing subterranean reservoirs, it usually is possible to recover only minor portions of the original oil in place by the so-called primary recovery methods which utilize only the natural forces in the reservoir. In order to increase the production of oil from subterranean reservoirs, resort has been taken to a variety of supplemental (secondary) recovery techniques. The most widely used supplemental technique is waterflooding, which involves the injection of water into the reservoir. As the water moves through the reservoir, it acts to displace oil therein toward a production system comprising one or more wells through which the oil is recovered.

It has long been recognized that factors such as the interfacial tension between the injected water and the reservoir oil, the relative mobilities of the reservoir oil and injected water, and the wettability characteristics of the rock surfaces within the reservoir are factors which influence the amount of oil recovered by waterflooding. Thus, it has been proposed to add surfactants to the flood water in order to lower the oil-water interfacial tension and/or to alter the wettability characteristics of the reservoir rock. Also, it has been proposed to add viscosifiers such as polymeric thickening agents to all or part of the injected water in order to increase the viscosity thereof, thus decreasing the mobility ratio between the injected water and oil and improving the sweep efficiency of the waterfood.

Surfactants used for enhanced oil recovery, particularly brine tolerant surfactants, are very expensive. Such surfactants tend to be absorbed by the rocks and clays in the reservoir, thus depleting their concentration in the waterflood fluid and diminishing their effectiveness by unfavorably increasing oil-water interfacial tension. A way to reduce absorptive loss is to use cheaper chemicals, i.e., sacrificial agents, that are absorbed on the rock, leaving the surfactant relatively less absorbed and free for its intended purpose.

The addition of various compounds to enhanced oil recovery fluids to reduce absorptive loss of surfactants to rock is not a new concept. Compounds which have been found to be effective include sodium phosphates (Roszelle U.S. Pat. No. 3,688,844), sodium silicates [P. Somasundaran and H. S. Hanna, *Society of Petroleum Engineers*, paper 7059, (1978)] and lignosulfonates [Kalfoglou U.S. Pat. No. 4,000,779 and Anon., *Paper Trade Journal*, 163, 21 (1979)]. These compounds were selected for their cheapness and effectiveness. However, it has been found that certain low molecular weight heterocyclic methanesulfonates of the present invention are even more effective than the most effective of the above named compounds, namely, the lignosulfonates.

Particular sacrificial agents according to the present invention are of the formula

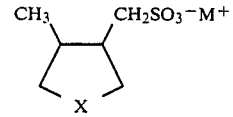

where:
(i) X is selected from the group consisting of O, S,

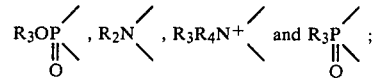

(ii) M is selected from the group Na, K, Li and $NH_4$; and
(iii) $R_2$ is selected from the group consisting of hydrogen, methyl, ethyl, n-propyl and i-propyl; and
(iv) $R_3$ and $R_4$ are the same or different and are selected from the group consisting of methyl, ethyl, n-propyl, and i-propyl, provided that M may be absent when X is $R_3R_4N^+$.

The method of this invention pertaining to sacrificial agents is applicable as an adjuvant to waterflood operations. It is primarily adapted to secondary recovery of light oils by waterflooding, but could be useful as a supplement to thermal recovery, such as by fireflooding, of heavy oils.

The method is carried out in a subterranean reservoir that is penetrated by spaced apart injection and production systems extending from the surface of the earth into the oil-bearing formation. The injection system comprises one or more wells into which are introduced fluids. The production system comprises one or more wells from which product is recovered. The wells in the injection and production systems are spaced apart and can be arranged in any desired pattern, such patterns being well known in waterflood operations. For example, the pattern can comprise a central injection well and a plurality of recovery wells spaced radially about the injection well.

The aqueous fluid used in the method of this invention pertaining to sacrificial agents is water or brine. An ideal source of brine is connate water previously obtained in production from the formation. The aqueous fluid may contain surfactants, such as anionic surface active agents, and may contain viscosifiers, such as polymeric thickening agents.

Any surfactant known in the art which will lower the interfacial tension between the injected aqueous solution and the reservoir oil can be used. More generally used are anionic alkali metal or ammonium sulfonates. Typical surfactants include petroleum sulfonates, alkylphenoxypoly(ethyleneoxy)propane sulfonates, and alkoxypoly(ethyleneoxy)propane sulfonate. Ordinarily the concentration of surfactant used will be between about 0.01 percent and about one percent. The alkoxy- or alkylphenoxy-polyethyleneoxypropane sulfonates will generally have 8–30 carbon atoms in the alkyl group, straight chain or branched, and 3–6 ethyleneoxy groups.

The addition of from about 0.3 to about 6% by weight of the sacrificial agents of the present invention, based upon the weight of the entire fluid to enhanced oil recovery fluids not only reduces adsorptive loss but causes oil to be produced by such fluids at an earlier stage in the injection thus reducing the cost of the process.

Surfactants for enhanced oil recovery and, in particular, brine tolerant surfactants are an expensive part of any enhanced oil recovery fluid. Consequently any inexpensive chemical which can reduce the amount of surfactant required can reduce the cost of the fluid. Since substantial amounts of time are required between the time an enhanced oil recovery fluid is injected and the time oil is produced a chemical which forces earlier production of oil can reduce costs simply by reducing the cost of borrowed money.

To illustrate the efficiency of sacrificial agents according to the present invention, three oil recovery experiments were carried out. In each case a six foot long glass column was packed with 160 g Berea sand, evacuated, filled with brine, the brine displaced with crude oil until no more oil was produced, then the oil displaced by brine until no more oil was produced. All solutions were flowed at 1.5 ml/hr. The brine contained 16.6% solids with the following composition:
NaCl = 13.2%
MgCl$_2$ = 0.72%
CaCl$_2$ = 2.62%

In each experiment a surfactant solution consisting of 0.525% sulfonate A and 0.175% alcohol B was injected continuously.

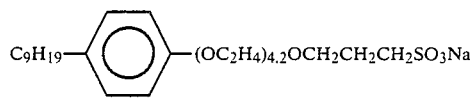

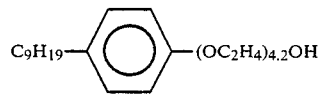

The amount of oil produced was determined volumetrically and the concentration of the surfactant A was determined by injecting produced aqueous solutions onto a Whatman ODS high pressure liquid chromatographic (HPLC) column. The effluent from the HPLC column was analyzed at 280 nm while the composition of the eluting solvent was varied linearly from 1.5 ml/min H$_2$O to 1.5 ml/min CH$_3$OH. The surfactant B had an elution time of 9.4 minutes.

In each case the weight of surfactant absorbed was determined by comparison of the concentration of surfactant produced to the concentration expected under conditions of plug flow and no absorption. The results of these experiments are set forth in Examples 4–7 as follows.

EXAMPLE 4

A control experiment was carried out as described above with no added sacrificial agents. The amount of surfactant absorbed was determined to be 450 mg. The production profiles for oil and surfactant in this experiment are shown in FIGS. 1 and 2.

EXAMPLE 5

An oil recovery experiment was carried out as described above but 3% ERA-4, a lignosulfonate from American Can Corporation, was added to the surfactant solution as a sacrificial chemical. The amount of surfactant absorbed was determined to be 365 mg, a reduction of 19%.

EXAMPLE 6

An oil recovery experiment was carried out as described above but 3% of a compound of the formula

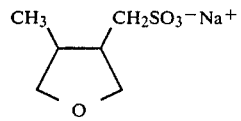

was added to the surfactant solution as a sacrificial chemical. The amount of surfactant absorbed was determined to be 280 mg, a reduction of 38% over the control. The production profiles for oil and surfactant are also shown in FIGS. 1 and 2 and they show quite clearly that the additive caused both reduced absorption and earlier oil production.

EXAMPLE 7

An oil recovery experiment was carried out as described above but 3% sodium 3-hydroxypropanesulfonate was added to the surfactant solution as a sacrificial chemical. The amount of surfactant absorbed was determined to be 410 mg, within experimental error of the control.

SURFACTANTS

Certain compounds of the present invention are felt to be particularly useful as surfactants in enhanced oil recovery fluids. More particularly, certain of these pyrrolidinium methanesulfonates are brine tolerant surfactants capable of producing low interfacial tensions between water and oil with or without an alcohol cosurfactant in the presence of salt concentrations, e.g., from 25% or less total salt and divalent ion concentrations from 200-20,000 ppm. These pyrrolidinium methanesulfonates have the formula

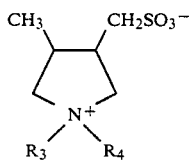

where $R_3$ and $R_4$ may be the same or different and may be alkyl (including alkylaryl) or aryl, provided that $R_3$ and $R_4$ contain together at least ten (e.g., 10-20) carbon atoms. Examples of alcohol cosurfactants include $C_4$-$C_7$ alcohols, especially, hexanol.

Various types of amphoteric surfactants are known. One type is described in the Maddox et al U.S. Pat. No. 3,939,911 and is represented as follows:

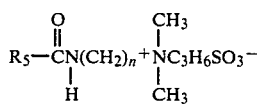

Another type of amphoteric surfactant is described in the Wilson et al U.S. Pat. No. 4,193,452 and is represented as follows:

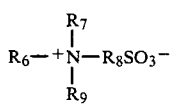

The above-illustrated surfactants of the Maddox et al Patent are to be used in conjunction with at least two other surfactants, and the above-illustrated surfactants of the Wilson et al Patent are to be used in conjunction with alcohol co-surfactant.

The surprising solubility properties of surfactants according to the present invention are revealed by comparing properties of a compound of the present invention according to the formula

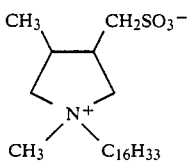

with properties of a compound according to the Wilson et al U.S. Pat. No. 4,193,452 according to the formula

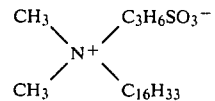

This comparison is described in the following examples:

EXAMPLE 8

Solubilities were measured by attempting to dissolve 2% weight/volume of sulfonate in a brine containing NaCl to $CaCl_2$ to $MgCl_2$ in weight ratio 13.2:2.6:0.8 over a total solids range of 0 to 28%. The compound of the present invention was soluble to 2% over this entire range while the compound of the Wilson et al Patent was only soluble in a narrow range from 12 to 19% total dissolved solids. The compound of the present invention could be dissolved to 10% over the range 0-20% total dissolved solids while the compound of the Wilson et al Patent could not be dissolved at such a high concentration at any brine concentration. The increased solubility due to the pyrrolidinium group is all the more unexpected when it is realized that the compound of the present invention contains a total of 23 carbon atoms compared to 21 for the compound of the Wilson et al Patent. An increase in carbon atoms would ordinarily be expected to produce a decrease in water solubility.

To demonstrate the surfactant properties of surfactants of the present invention, surfactants were dissolved in brines whose $NaCl:CaCl_2:MgCl_2$ compositions were as described above and the interfacial tensions of the surfactant solution measured against crude oil by the spinning drop method described by Wade in *Adsorption at Interfaces*, ACS Symp #8, pp 234-47 (1975). These procedures are discussed in the following Examples 9-11.

EXAMPLE 9

A solution containing 12% brine, 2% surfactant of the formula and 0.57% hexanol was equilibrated with oil and the interfacial tension measured against crude oil. The interfacial tension was 33 millidyne/cm.

EXAMPLE 10

Example 10 was the same as Example 9, but 16.6% brine was used and the interfacial tension was 6 millidyne/cm.

EXAMPLE 11

Example 11 was the same as Example 9, but the brine was 22% and the surfactant had the formula

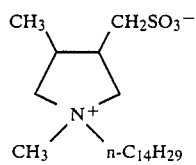

The interfacial tension was 13 millidyne/cm.

The compounds of the present invention may be useful in fields other than the enhanced recovery of oil. For example, these compounds may have utility as synthetic intermediates particularly those in which X is a heteroatom since this method represents an extremely efficient way of synthesizing cis-3,4-substituted five membered ring heterocycles, an otherwise difficult class of compounds to synthesize. Also, oil soluble compounds where X is O, S,

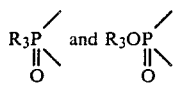

are believed to be antirust agents in lubricating oils.

The patents and literature articles cited herein are hereby expressly incorporated herein by reference.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A compound according to the formula

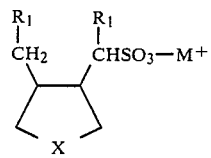

wherein:
(i) X is selected from the group consisting of O and S;
(ii) $R_1$ is selected from the group consisting of hydrogen and unsubstituted $C_1$–$C_3$ alkyl; and
(iii) M is selected from the group consisting of Na, K, Li and $NH_4$.

2. A compound according to claim 1, wherein:
(i) X is selected from the group consisting of O and S; and
(ii) $R_1$ is hydrogen.

3. A compound according to claim 2, wherein
(i) $R_1$ is hydrogen;
(ii) X is O; and
(iii) M is Na.

* * * * *